United States Patent [19]
Yates et al.

[11] Patent Number: 5,708,363
[45] Date of Patent: Jan. 13, 1998

[54] LIQUID CONDUCTIVITY MEASUREMENT SYSTEM USING A VARIABLE-FREQUENCY AC VOLTAGE

[75] Inventors: Ronald J. Yates, Long Beach; Martin M. Munzer, Alhambra; Frederic D. Hook, Fontana, all of Calif.

[73] Assignee: Signet Scientific Company, El Monte, Calif.

[21] Appl. No.: 543,504

[22] Filed: Oct. 16, 1995

[51] Int. Cl.$^6$ .................................... G01N 27/02
[52] U.S. Cl. .................... 324/442; 324/707; 324/603
[58] Field of Search ........................ 324/442, 436, 324/707, 619, 603

[56] References Cited

U.S. PATENT DOCUMENTS

| | | | |
|---|---|---|---|
| 2,771,579 | 11/1956 | Ruge . | |
| 3,479,590 | 11/1969 | Henderson . | |
| 3,528,287 | 9/1970 | Melcher . | |
| 3,906,353 | 9/1975 | Murdock | 324/442 |
| 4,264,860 | 4/1981 | Thebault . | |
| 4,408,282 | 10/1983 | Hof . | |
| 4,602,338 | 7/1986 | Cook . | |
| 4,922,182 | 5/1990 | Cox . | |
| 4,935,692 | 6/1990 | Wakasugi . | |
| 5,260,663 | 11/1993 | Blades | 324/442 |
| 5,504,430 | 4/1996 | Andersson | 324/442 |

Primary Examiner—Ernest F. Karlsen
Assistant Examiner—Jose M. Solis
Attorney, Agent, or Firm—Sheppard, Mullin, Richter & Hampton; J. R. Brueggemann

[57] ABSTRACT

A liquid conductivity measurement system is disclosed that accurately measures a liquid's conductivity over a range spanning at least several orders of magnitude using just a single sensor, but minimizing the adverse effects of capacitive and other non-linear factors on the conductivity measurement. The system includes a sensor having two spaced-apart electrodes immersed in the liquid and a drive signal source that applies to the sensor an ac electrical signal having a selected frequency and predetermined magnitude. A voltage detector monitors a sensor voltage signal across the sensor's two electrodes and produces a measurement of the liquid's conductivity. The drive signal source is configured to iteratively adjust the frequency of the ac electrical signal based on the sensor voltage signal, to optimize the liquid's conductivity measurement.

20 Claims, 2 Drawing Sheets

LIQUID CONDUCTIVITY MEASUREMENT SYSTEM USING A VARIABLE-FREQUENCY AC VOLTAGE

BACKGROUND OF THE INVENTION

This invention relates generally to industrial liquid conductivity measurement systems and, more particularly, to systems that measure the conductivity of a liquid over a large dynamic range.

In industrial systems, certain processes require a liquid of a known quality or purity to be used in, or to result from, the process. Therefore, it is very important that such characteristics of the liquid be monitored. Often, the liquid's pH and conductivity (or resistivity) are good indicators of whether the liquid meets certain quality standards. For example, pure water allows very little electrical current to flow through it, and therefore, pure water has a very low conductivity. However, water having dissolved ions exhibits a significantly increased conductivity over that of pure water, because the dissolved ions act as charge carriers. Thus, the conductivity measurement provides a good basis for monitoring water purity.

A liquid's conductivity can be monitored by placing a sensor having two electrodes within the liquid, applying a known dc voltage across the electrodes, and measuring the resulting dc current. Although, a conductivity measurement cannot identify the ions in the water, it can determine the concentration of ions in the water, because the resulting dc current is indicative of the concentration of positive dissolved ions migrating toward the negative electrode and/or negative dissolved ions migrating toward the positive electrode. However, the dc current causes electrolysis which, depending on the elements involved, can erode or cause material collection on the electrodes.

Some liquid conductivity monitoring systems reduce the electrolysis problem by applying a square wave to the sensor instead of a dc voltage. However, capacitive effects due to the cell's construction and the solution's reaction to the square wave can distort the square wave, making it difficult to accurately measure the liquid's conductivity.

The voltage applied across the electrodes and the resulting current through the liquid can be used, via Ohm's law, to determine the conductance between the electrodes. The conductance between the electrodes is related to the liquid's conductivity by a normalization factor called the cell constant, K. More specifically, the conductivity σ is equal to the conductance G multiplied by the cell constant K (i.e., σ=G·K). The size and spacing between the electrodes define the cell constant. The cell constant K for two parallel plate electrodes is defined as the distance d between the plates divided by the area A of the plates (i.e., K=d/A). Accordingly, for a liquid of a given conductivity, changing the cell constant results in a corresponding change in the magnitude of the conductance measured between the electrodes. However, for practical considerations, the sensor is often placed in a voltage divider network with a source resistor, and the sensor's cell constant often is selected to provide a sensor resistance measurement (i.e., the reciprocal of the conductivity) that is within an order of magnitude of the resistance of the source resistor.

In the past, some laboratory conductivity instruments have measured conductivity over an extended range of conductivity values by dividing the extended range into several decade ranges and providing, for each decade range, a sensor having a predetermined cell constant and by using a preset measurement frequency for each decade range. However, using multiple sensors having different cell constants to provide an extended conductivity measurement range frequently is impractical in industrial applications, because the sensor is permanently installed at a remote location.

Further, the preset measurement frequency associated with a given decade range is set to one fixed frequency, which frequency often is selected to provide a most accurate measurement for a value lying only at the center of the decade range. However, because of nonlinear effects, the measurements associated with values lying at the edges of the decade range necessarily are not as accurate as measurements associated with values lying in the center of the decade range. Further, such laboratory instruments require a coaxial cable having a fixed length between the sensor and the measurement circuit, to compensate for capacitive effects.

Accordingly, there is a need for a conductivity measurement system that accuracy monitors conductivity over a range of several decades that eliminates the need for multiple sensors and that minimizes any capacitive or other non-linear effects detrimental to accuracy. The present invention satisfies this need.

SUMMARY OF THE INVENTION

The present invention is embodied in an apparatus, and related method, that measures the conductivity of a liquid over a range of several decades while eliminating the need for multiple sensors and minimizing any capacitive or other non-linear effects that can lead to inaccuracies. The apparatus includes a sensor having two spaced-apart electrodes disposed in contact with the liquid whose conductivity is to be measured and a drive signal source that applies to the sensor an ac electrical signal having a selected frequency and predetermined magnitude. A voltage detector monitors a sensor voltage signal across the sensor's two electrodes and produces a measurement of the liquid's conductivity. The drive signal source is configured to iteratively adjust the frequency of the ac electrical signal based on the sensor voltage signal, to optimize the measurement of the liquid's conductivity.

More particularly, the drive signal source includes a variable-frequency voltage generator that produces a sine wave voltage signal having a predetermined ac voltage and further includes a source resistance connected in series with that voltage generator. The apparatus further includes a processor that determines a resistance through the sensor based on the ac voltage level of the sine wave voltage signal, the source resistance, and the measured sensor voltage signal. The processor then provides the measurement of the liquid's conductivity based on the determined sensor resistance and a cell constant that is established for the particular sensor being used.

In a more detailed feature of the invention, the source resistance coupled in series with the variable-frequency voltage generator is selected from a plurality of source resistors having resistances that vary over orders of magnitude. The processor is configured to iteratively select from among the plurality of source resistors, based on the determined resistance through the sensor, such that the source resistance is within an order of magnitude of the sensor's resistance.

In another more detailed feature of the invention, the processor includes a lookup table that indicates a desired relationship between the frequency of the ac electrical signal and the value of the measured sensor resistance. The processor controls the drive signal source to operate at frequency selected from the lookup table based on the measured sensor resistance. For particular sensor resistance measurements that lie between resistance values contained in the lookup table, the processor calculates the desired frequency using linear interpolation.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
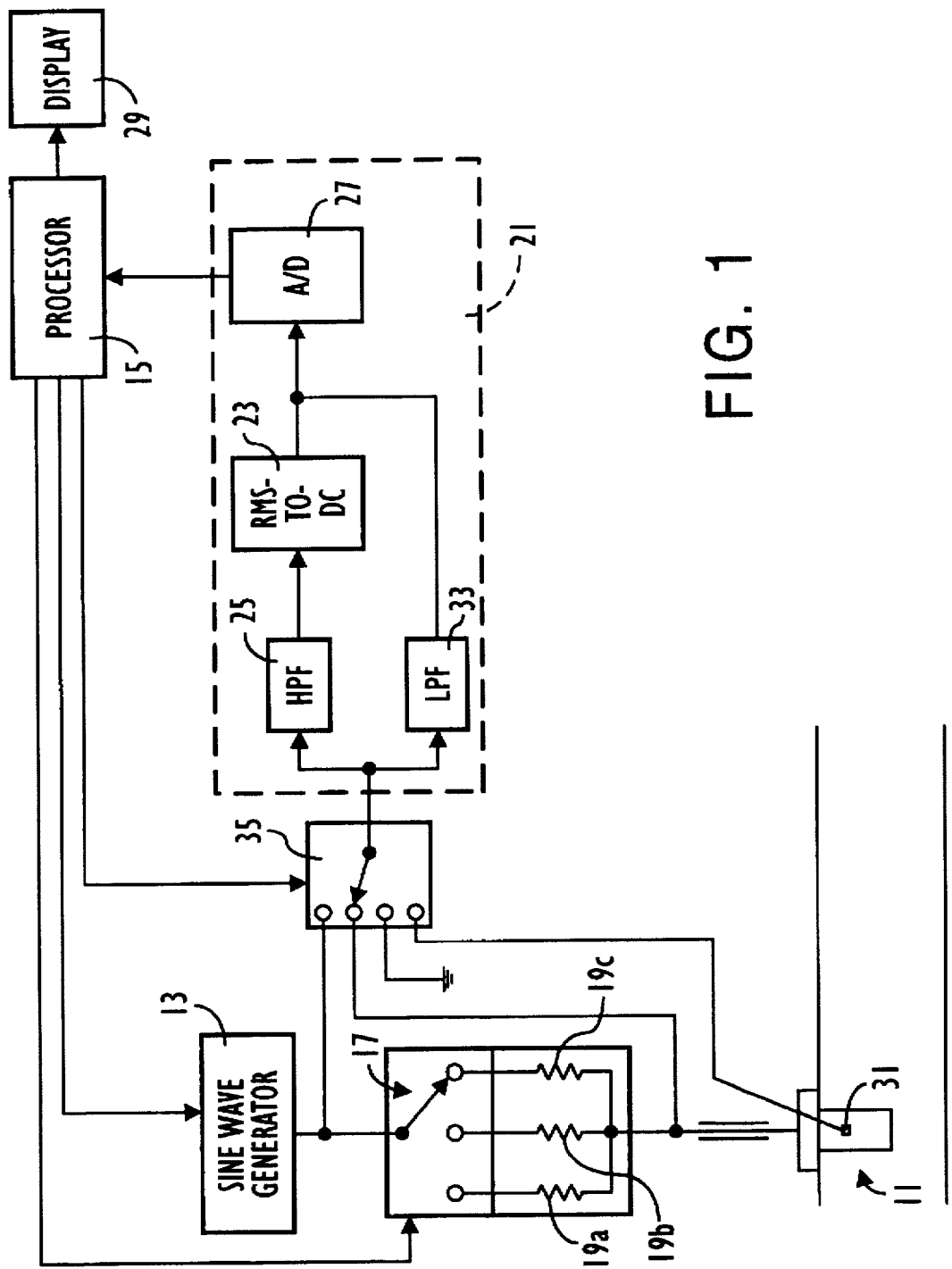
FIG. 1 is a block diagram of a conductivity measurement system, in accordance with the present invention, for measuring the conductivity of a liquid.

As shown in the exemplary drawings, and in particular in FIG. 1, the present invention is embodied in an apparatus for measuring the conductivity of a liquid using an ac source signal applied a sensor contacting the liquid. The frequency of the ac source signal is selected, based on a voltage signal measured across the sensor 11, to compensate for certain capacitive and nonlinear effects and to improve the accuracy of the conductivity measurement. The apparatus operates over a range spanning several decades, and several frequencies are available for selection within each decade.

Figure 2:
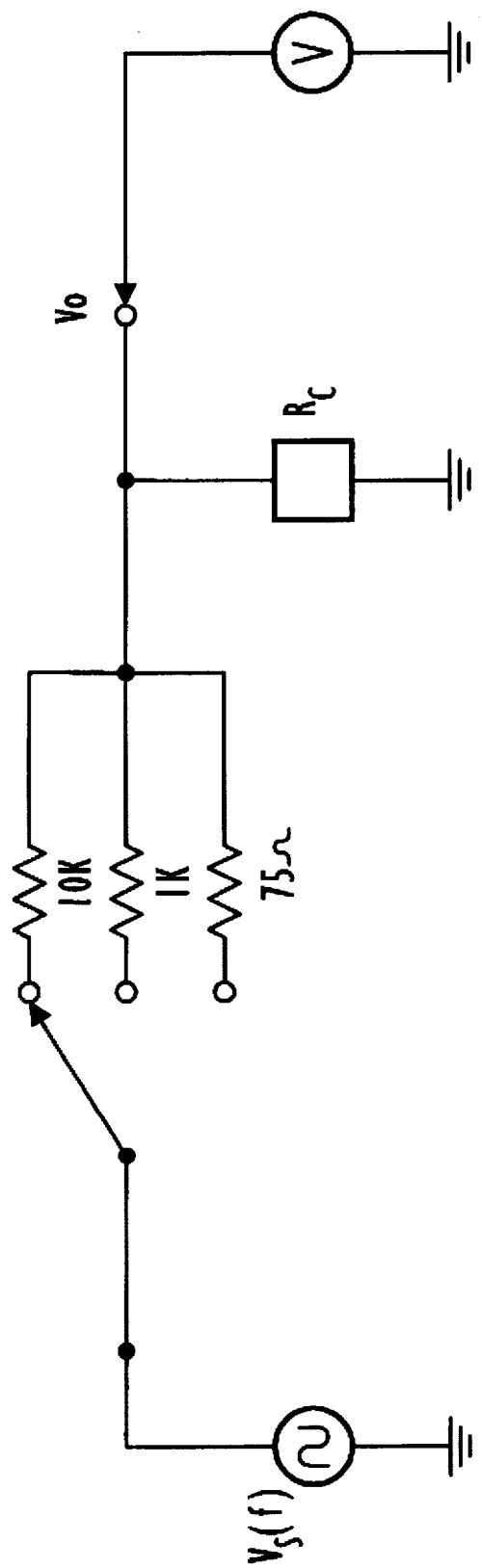
FIG. 2 is a schematic diagram showing, in simplified form, the electrical association of the conductivity measurement system of FIG. 1.

The ac source signal is generated by a sine-wave voltage generator 13 connected in series with a selectable source resistance Rs (FIG. 2). The sine wave voltage generator produces a voltage signal Vs having a selectable frequency between 500 Hz and 50 KHz. The voltage generator sets the frequency in response to a program word received from a processor 15. The resistance value of the source resistance Rs is set by a three-position switch 17, controlled by the processor, that selects between a 75 ohm resistor 19a, a 1K resistor 19b, and 10K resistor 19c. These three resistance values differ from each other by about one order of magnitude. The source resistance is connected in series with the sensor 11, to form a voltage-divider circuit. A voltage detector 21 monitors the sensor's output voltage signal Vo that results from the applied ac source signal. The resistance Rc through the sensor is calculated using the sensor's output voltage and the known values of the voltage signal Vs and the source resistance.

The resistance Rc through the sensor is related to the voltage measured across the sensor by the formula, Rc= (Vo·Rs)/(Vs-Vo). If Rs>>Rc or Rs<<Rc, then a small change in the output voltage Vo results in a large change in the measured resistance Rc. Accordingly, the processor 15 selects the particular one of the three source resistors 19a, 19b and 19c that has resistance value within an order of magnitude of the measured probe resistance Rc. This improves the accuracy of the resistance measurement and extends the sensor's operating range. The liquid's conductivity (or resistivity) is related to the calculated resistance through the sensor by the sensor's cell constant.

To further optimize the accuracy of the conductivity or resistivity measurement, the apparatus uses an iterative technique to select a source resistor Rs and a source frequency fs. In the iterative technique, the apparatus first measures the liquid's conductivity using the 10K resistor 19c as the source resistance Rs and a frequency of 500 Hz as the source frequency fs. It will be recognized that this initial source resistance Rs and initial source frequency fs might not be the particular values that provide the most accurate conductivity measurement. However, selecting these values will minimize some stray capacitance effects and provide a reasonable starting point.

Based on the resistance measurement Rc, the processor 15 then selects the particular source resistance Rs from the three resistors 19a, 19b and 19c that is within an order magnitude of that resistance Rc. The processor incorporates a small amount of hysteresis in selecting the source resistor to avoid frequent switching of the source resistance when the resistance measurement is near 1K or 10K. Thus, for example, if the resistance measurement is performed using the 10K resistor 19c and the measured resistance Rc lies below 800 ohms, then the 75-ohm resistor 19a is selected for the next measurement. If the measured resistance Rc lies in the range of 800 ohms to 8K ohms, then the 1K resistor 19b is selected for the next measurement. Further, if the resistance measurement is performed using the 1K resistor 19b and the measured resistance Rc lies below 800 ohm, then the 75-ohm resistor 19a is selected for the next measurement. However, if the measured resistance lies above 10K, then the 10K resistor 19c is selected. Otherwise, the 1K resistor 19b remains selected for the next measurement. Finally, if the resistance measurement is performed using the 75-ohm resistor 19a and the measured resistance Rc lies above 10K, then the 10K resistor 19c is selected and if the measured resistance Rc lies above 1K, then the 1K resistor 19b is selected. Otherwise, the 75-ohm resistor 19a remains selected for the next measurement.

Using a lookup table shown in Table I below, the apparatus also iteratively adjusts the source frequency fs, based on the previous resistance measurement. For example, if the source resistance Rs selected for a particular measurement was 1K and the measured resistance Rc was 2.0K, then the processor source would select frequency fs for the next measurement to be 7500 Hz.

TABLE I

| Rs = 10K | | Rs = 1K | | Rs = 75Ω | |
|---|---|---|---|---|---|
| Rc(meas) | fs(Hz) | Rc(meas) | fs(Hz) | Rc(meas) | fs(Hz) |
| 100K | 500 | 10K | 2000 | 1K | 10700 |
| 50K | 500 | 5K | 3000 | 500 | 11500 |
| 33.3K | 600 | 3.33K | 5000 | 333 | 38000 |
| 25K | 600 | 2.5K | 6500 | 250 | 42000 |
| 20K | 700 | 2.0K | 7500 | 200 | 50000 |
| 16.6K | 800 | 1.66K | 8000 | 166 | 50000 |
| 14.2K | 900 | 1.42K | 9500 | 142 | 50000 |
| 12.5K | 1000 | 1.25K | 10000 | 125 | 50000 |
| 10K | 1000 | 1K | 10500 | 100 | 50000 |

The conductivity measurement sequence is then repeated with the source frequency fs tracking the value of the last measured resistance Rc. Because it takes only about one second to perform each successive measurement sequence, the tracking error generally is very low. This is because, under normal conditions, the liquid's conductivity generally will vary only insignificantly in one second.

Interpolation is used to select a source frequency fs corresponding to a resistance measurement Rc that lies between the values listed in the table. Even though the relationship between the source frequency fs and the measured resistance Rc is nonlinear, the relationship between the adjacent entries in the lookup table is sufficiently linear for the table to provide a source frequency that will compensate for the nonlinearity. Thus, the tunable frequency generator 13 can be tuned to nearly any desired frequency, to compensate for nonlinearities across three orders of magnitude of measured sensor resistance, using only a relatively short lookup table.

The sine-wave generator 13 is driven by an internal 12-Megahertz crystal oscillator and it is programmed to select the desired output frequency using a 16-bit word provided by the processor. The output frequency is given by the equation $f_{out}=(f_{clk} \cdot D)/2^{23}$, where $f_{clk}=12$ Megahertz and D is the decimal value of the 16-bit word. The 16-bit word allows 65,536 steps, scaled between zero and 93,750 Hz, in the output frequency.

The sine wave generator 13 includes an accoupled operational amplifier to buffer its output signal. The magnitude of the voltage signal is selected to be either 0.9 volts peak-to-peak or 1.91 volts peak-to-peak.

The voltage detector 21 includes a root-mean-square (RMS) ac voltage-to-dc voltage converter 23, implemented using an integrated RMS-to-dc converter (AD737KN), available from Analog Devices, of Norwood, Mass. A 4.7 μF capacitor connected to the converter's output terminal minimizes the ripple on the converter's dc voltage output signal, while providing an acceptable settling times of 100 milliseconds or less. Detecting the RMS value of the sensor's output voltage is advantageous, because it eliminates the need to completely compensate for stray capacitances. Stray capacitances can cause a phase delay that can significantly distort the waveform of the output voltage signal resulting in an inaccurate voltage measurement in a voltage detector based on peak detection. The system of present invention compensates for the capacitance associated with a coaxial cable having a length of about 25 feet. However, because the system uses RMS detection, it still provides accurate conductivity measurements with a coaxial cable having a length between 15 and 50 feet, and it provides acceptable measurements with a cable having a length up to 100 feet, if reduced dynamic range is acceptable.

Preferably, a high-pass filter 25 is coupled between the sensor 11 and the input to the RMS-to-dc converter 23. The filter, with a cutoff frequency of about 100 Hz, provides 32 dB of damping at 60 Hz.

An analog-to-digital (A/D) converter 27 provides a digital word to the processor 15, representing the magnitude of the dc voltage on the converter's input terminal. The processor calculates the liquid's conductivity based on the sensor's output voltage and the known cell constant, and it provides a conductivity measurement reading on a display 29.

Traditionally, conductivity measurement readings are normalized to a 25° C. temperature compensated reading, expressed in units of micro-Siemens per centimeter. Accordingly, a thermistor 31, such as a platinum device, is integrated into the body of the sensor 11 and biased using a voltage divider circuit, to provide a dc-voltage signal Vt based on the sensor's temperature.

After the processor 15 calculates the raw conductivity and calculates the temperature based on the thermistor voltage signal Vt, the processor calculates the conductivity associated with 25° C. using the formula G(25° C.)=G(T)/[1+S (T-25)], where T is the measured temperature of the sensor and S is the compensation slope, normally about 2%.

Preferably, a low-pass filter 33 is coupled between the thermistor 31 and the A/D converter 27. The filter, with a cutoff frequency of about 10 Hz, provides 31 dB damping at 50 Hz.

A programmable multiplexer switch 35 selects between the ac source voltage signal Vs, the sensor's output voltage signal Vo, and the thermistor voltage Vt. For calibration purposes, the multiplexer switch can also select a zero voltage from a ground terminal. Between the multiplexer switch and the A/D converter 27, the ac signals pass through the high-pass filter 25, and thus the RMS-to-dc converter 25, and the dc signals pass through the dc filter 33.

One advantage of the system of the present invention is that conductivity sensors formed of 316 stainless steel can be used to accurately monitor a liquid's conductivity over a three-decade range. The sensor's cell geometry can be coaxial or symmetrical, depending on the desired cell constant and configuration. Typical cell constants are 0.1/cm, 1.0/cm, 10.0/cm, and 20.0/cm. The system, using a sensor with a 0.1/cm cell constant, can measure a liquid's conductivity down to 1 micro-Siemen and, using a sensor with a 20.0/cm cell constant can measure conductivity up to 200,000 micro-Siemen, with an accuracy of 2% of the reading.

Although the foregoing discloses the presently preferred embodiments of the present invention, it is understood that those skilled in the art may make various changes to the preferred embodiment shown without departing from the scope of the invention. The invention is defined only by the following claims.

We claim:

1. Apparatus for measuring the conductivity of a liquid, comprising:

a sensor having two spaced-apart electrodes disposed in a contact with the liquid;

a drive signal source that provides an ac electrical signal of a selected frequency across the two electrodes of the sensor; and a voltage detector that is coupled to the sensor and that monitors a sensor voltage signal across the two electrodes, the magnitude of the sensor voltage signal providing a measurement of the liquid's conductivity;

wherein the drive signal source is configured to iteratively adjust the frequency of the ac electrical signal based on the sensor voltage signal, to optimize the measurement of the liquid's conductivity.

2. Apparatus for measuring a liquid's conductivity as defined in claim 1, wherein the drive signal source includes:

a variable-frequency voltage generator that generates a sine-wave voltage signal having a predetermined ac voltage; and a source resistance coupled in series with the voltage generator, wherein the series combination of the voltage generator and the source resistance produces the predetermined ac electrical signal.

3. Apparatus for measuring a liquid's conductivity as defined in claim 2, wherein:

the spaced-apart electrodes of the sensor define a cell constant; and the apparatus further includes a processor that determines a resistance through the sensor based on the ac voltage of the sine-wave voltage signal, the source resistance, and the sensor voltage signal, and that provides the measurement of conductivity based on the resistance through the sensor and the cell constant.

4. Apparatus for measuring a liquid's conductivity as defined in claim 3, wherein:

the source resistance includes a plurality of source resistors having resistances that differ over at least two orders of magnitude; and the processor is configured to iteratively select from among the plurality of source resistors, based on the determined resistance through the sensor, such that the source resistance is within an order of magnitude of the sensor's resistance.

5. Apparatus for measuring a liquid's conductivity as defined in claim 3, wherein:

the processor includes a lookup table that indicates a desired relationship between the frequency of the ac electrical signal and the value of the measured sensor resistance; and the processor, using the lookup table, selects a frequency based on the sensor's resistance and controls the drive signal source to operate at the selected frequency.

6. Apparatus for measuring a liquid's conductivity as defined in claim 5, wherein the processor uses linear interpolation to calculate the frequency for a resistance value lying between the resistance values contained in the lookup table.

7. Apparatus for measuring a liquid's conductivity as defined in claim 2, wherein the voltage generator is configured to adjust the selected frequency in frequency steps of less than 100 Hz.

8. Apparatus for measuring a liquid's conductivity as defined in claim 2, wherein the voltage generator is configured to adjust the selected frequency in frequency steps of less than 10 Hz.

9. Apparatus for measuring a liquid's conductivity as defined in claim 2, wherein the voltage generator is configured to adjust the selected frequency substantially continuously over a frequency range from 500 Hz to 50 KHz.

10. Apparatus for measuring a liquid's conductivity as defined in claim 1, and further comprising a temperature monitor, integrated within the sensor, to measure the sensor's temperature.

11. Apparatus for measuring a liquid's conductivity as defined in claim 10, and further comprising means for normalizing the conductivity reading to a 25° C. temperature compensated conductivity reading.

12. A method for measuring the conductivity of a liquid, comprising:

providing a sensor having two spaced-apart electrodes that electrically contact the liquid;

applying an ac drive signal to the electrodes of the sensor, the ac drive signal having a predetermined initial frequency;

detecting the voltage across the sensor that results from the applied ac drive signal, such voltage constituting a measurement of the liquid's conductivity;

adjusting the frequency of the ac drive signal to a frequency selected to provide an accurate measurement for the liquid's conductivity;

applying the ac drive signal with the adjusted frequency to the sensor; and iteratively repeating the detecting, adjusting and applying steps.

13. A method as defined in claim 12, wherein:

the ac drive signal used in the steps of applying is sinusoidal; and the steps of applying include connecting a source resistance in series with the sensor.

14. A method as defined in claim 13, wherein the step of adjusting includes selecting the value of the source resistance.

15. A method as defined in claim 12, wherein the step of adjusting includes selecting the frequency by reference to a lookup table that indicates a desired relationship between the frequency of the ac drive signal and the measurement of the liquid's conductivity.

16. A method as defined in claim 15, wherein the step of adjusting includes interpolating between discrete values included in the lookup table.

17. A method as defined in claim 12, wherein the step of adjusting includes adjusting the selected frequency in frequency steps of less than 100 Hz.

18. A method as defined in claim 12, wherein the step of adjusting includes adjusting the selected frequency in frequency steps of less than 10 Hz.

19. A method as defined in claim 12, wherein the step of adjusting includes adjusting the selected frequency substantially continuously over a frequency range from 500 Hz to 50 KHz.

20. A method as defined in claim 12, and further comprising normalizing the successive conductivity measurements to 25 degrees C.

* * * * *